(12) United States Patent
Nakamoto et al.

(10) Patent No.: US 8,124,138 B2
(45) Date of Patent: Feb. 28, 2012

(54) COMPOSITION FOR PREVENTION AND/OR TREATMENT OF PRURITUS CONTAINING ACACIA BARK DERIVATIVE

(75) Inventors: Yusho Nakamoto, Hatsukaichi (JP); Keiko Ono, Hatsukaichi (JP)

(73) Assignee: Mimozax Co., Ltd., Hatsukaichi-shi (JP)

( * ) Notice: Subject to any disclaimer, the term of this patent is extended or adjusted under 35 U.S.C. 154(b) by 154 days.

(21) Appl. No.: 12/376,905

(22) PCT Filed: Aug. 10, 2006

(86) PCT No.: PCT/JP2006/315866
§ 371 (c)(1),
(2), (4) Date: Feb. 9, 2009

(87) PCT Pub. No.: WO2008/018141
PCT Pub. Date: Feb. 14, 2008

(65) Prior Publication Data
US 2010/0247690 A1 Sep. 30, 2010

(51) Int. Cl.
*A01N 65/00* (2009.01)
(52) U.S. Cl. .................................................. 424/725
(58) Field of Classification Search .................. None
See application file for complete search history.

(56) References Cited

U.S. PATENT DOCUMENTS

| | | | |
|---|---|---|---|
| 5,629,338 A | 5/1997 | Okuda et al. | |
| 6,290,993 B1 | 9/2001 | Anderson et al. | |
| 6,294,190 B1 | 9/2001 | Nakahara et al. | |
| 7,514,469 B2 * | 4/2009 | Jia ................................. | 514/456 |
| 2003/0180402 A1 | 9/2003 | Jia et al. | |
| 2003/0232099 A1 | 12/2003 | Pan et al. | |
| 2004/0186062 A1 | 9/2004 | Burnett et al. | |
| 2005/0095332 A1 | 5/2005 | Stanley | |
| 2006/0204599 A1 | 9/2006 | Wheat | |
| 2008/0124415 A1 | 5/2008 | Tanaka et al. | |

FOREIGN PATENT DOCUMENTS

| | | |
|---|---|---|
| CN | 1753681 A | 3/2006 |
| FR | 2 710 533 A1 | 4/1995 |
| JP | 64-025726 U | 2/1989 |
| JP | 3-287507 A | 12/1991 |
| JP | 6-065074 A | 3/1994 |
| JP | 7-138178 A | 5/1995 |
| JP | 7-300422 A | 11/1995 |
| JP | 8-259557 A | 10/1996 |
| JP | 9-291039 A | 11/1997 |
| JP | 10025238 A | 1/1998 |
| JP | 11-005975 A | 1/1999 |
| JP | 11-180888 A | 7/1999 |
| JP | 2000-044472 A | 2/2000 |
| JP | 2000-073056 A | 3/2000 |
| JP | 2001-098264 A | 4/2001 |
| JP | 2002-010753 A | 1/2002 |
| JP | 2002-051735 A | 2/2002 |
| JP | 2002-275076 A | 9/2002 |
| JP | 2003-519092 A | 6/2003 |
| JP | 2003-313138 A | 11/2003 |
| JP | 2003-342185 A | 12/2003 |
| JP | 2004-008215 A | 1/2004 |
| JP | 2004-024054 A | 1/2004 |
| JP | 2004-075579 A | 3/2004 |
| JP | 2004-091464 A | 3/2004 |
| JP | 2004-217559 A | 8/2004 |
| JP | 2004-300117 A | 10/2004 |
| JP | 2004532811 T | 10/2004 |
| JP | 2004-323362 A | 11/2004 |
| JP | 02004352639 | * 12/2004 |
| JP | 2004352639 A | 12/2004 |
| JP | 2005-239559 A | 9/2005 |
| JP | 2005-529898 A | 10/2005 |
| JP | 2006-232781 A | 9/2006 |
| JP | 2006-232782 A | 9/2006 |
| WO | WO 03/092599 A2 | 11/2003 |
| WO | WO 2005/020932 A2 | 3/2005 |
| WO | WO 2006/003909 A1 | 1/2006 |

OTHER PUBLICATIONS

*Acacia meransii*, 5 pages 2010.*
Taguchi et al., "Evaluation of antipruritic effect of apple polyphenols using a new animal model of pruritus." J. Tokyo Med. Univ., Feb. 15, 2002, vol. 60, No. 2, pp. 123-129.
Ohara et al., "Condensed Tannins from *Acacia mearnsii* and Their Biological Activities." Mokuzai Gakkaishi, 1994, vol. 40, No. 12, pp. 1363-1374.
Seiji Ohara, "Juhi Tannin no. Kagaku Tokusei to Yoto Kaihatsu." APAST, 2003, vol. 13, No. 1, pp. 7-11.
Takagi et al., "Tyrosinase inhibitory activity of proanthocyanidins from woody plants." J. Wood Sci., 2003, vol. 49, No. 5, pp. 461-465.
Ohara "Chemical Properties and Application Development of Bank Tannin", APAST, vol. 13, No. 1 (Jan. 2003) pp. 7-11 (and English Translation, pp. 1-10).
Botha et al., "Condensed tannins: direct synthesis, structure, and absolute configuration of four biflavonoids from black wattle bark ('mimosa') extract," J Chem Soc, Chem Commun, 1978, vol. 16, pp. 700-702.
Chang et al., "Antioxidant activity of extracts from *Acacia confusa* bark and heartwood," J Agric Food Chem, Jul. 2001, vol. 49, No. 7, pp. 3420-3424. Duan et al., "Condensed tannins from steamed *Acacia mearnsii* bark," Holzforschung, May 2005, vol. 59, No. 3, pp. 289-294.
Fragrance Journal, 1995, 23(10), pp. 96-102.
Haridas et al., "Avicins: triterpenoid saponins from *Acacia victoriae* (Benthan) induce apoptosis by mitochondrial perturbation," PNAS, May 8, 2001, vol. 98, No. 10, pp. 5821-5826.
Ishida et al., "Solid sampling technique for direct detection of condensed tannins in bark by matrix-assisted laser desorption/ionization mass spectrometry," Rapid Commun Mass Spectrom, 2005, vol. 19, No. 5, pp. 706-710.
Japanese Office Action issued in Japanese Patent Application No. 2005-132746 on Aug. 2, 2011.

(Continued)

*Primary Examiner* — Michael Meller
(74) *Attorney, Agent, or Firm* — Birch, Stewart, Kolasch & Birch, LLP

(57) ABSTRACT

It is intended to provide a composition which is useful in preventing and/or treating pruritus. The composition is a composition for the prevention and/or treatment of pruritus, containing an *acacia* bark derivative.

8 Claims, No Drawings

OTHER PUBLICATIONS

Liu et al., "Antidiabetic effect of Pycnogenol French maritime pine bark extract in patients with diabetes type II," Life Sci, Oct. 8, 2004, vol. 75, No. 21, pp. 2505-2513.

Properties, Composition, Reactions and Industrial Applications of Mimosa Extract, African Territories Wattle Industry Fund Limited, Jan. 1980, London, England.

Seigler, "Phytochemistry of Acacia-sensu lato," Biochemical Systematics and Ecology, 2003, vol. 31, No. 8, pp. 845-873.

U.S. Office Action issued in U.S. Appl. No. 12/376,895 on Jan. 6, 2011.

U.S. Office Action issued in U.S. Appl. No. 12/376,895 on May 2, 2011.

U.S. Office Action issued in U.S. Appl. No. 12/376,895 on Nov. 2, 2010.

U.S. Office Action issued in U.S. Appl. No. 12/376,902 on Jan. 3, 2011.

U.S. Office Action issued in U.S. Appl. No. 12/376,902 on Jun. 15, 2011.

U.S. Office Action issued in U.S. Appl. No. 12/376,902 on Oct. 20, 2010.

U.S. Office Action issued in U.S. Appl. No. 12/376,904 on Aug. 31, 2010.

U.S. Office Action issued in U.S. Appl. No. 12/376,904 on Feb. 16, 2011.

U.S. Office Action issued in U.S. Appl. No. 12/376,904 on Jun. 17, 2011.

U.S. Office Action issued in U.S. Appl. No. 12/376,939 on Jan. 10, 2011.

U.S. Office Action issued in U.S. Appl. No. 12/376,939 on Jul. 21, 2011.

U.S. Office Action issued in U.S. Appl. No. 12/376,939 on Oct. 7, 2010.

Wassel et al., "Phyochemical examination and biological studies of *Acacia nilotica L. Willd* and *Acacia farnesiana L. Willd* growing in Egypt," Egyptian Journal of Pharmaceutical Sciences, 1992, vol. 33, Nos. 1-2, pp. 327-340.

* cited by examiner

COMPOSITION FOR PREVENTION AND/OR TREATMENT OF PRURITUS CONTAINING ACACIA BARK DERIVATIVE

TECHNICAL FIELD

The present invention relates to a composition derived from a tree belonging to the genus *Acacia* for the prevention and/or treatment of pruritus, and to uses of this composition as a food, an animal feed material, a medicine and a quasi-drug.

BACKGROUND ART

Pruritus, or itching, is an extremely uncomfortable condition that can cause problems during the course of daily life. Pruritus is caused by various factors, including skin diseases such as atopic dermatitis, senile pruritus, urticaria, eczema, insect bites, dry skin or rashes, kidney disease, diabetes, collagen diseases, aging, and heat and cold stimuli. There are also cases in which scratching a pruritic site may lead to a vicious cycle in the form of further exacerbating symptoms or causing more intense itching.

For example, atopic dermatitis is known to be easily exacerbated by external stimuli such as perspiration, scratching or rubbing, and itching is the most important treatment objective.

Thus, it is important to provide treatment that first suppresses itching in order to treat the skin diseases as listed above.

Various medicinal and topical treatment methods are known for the treatment of pruritus. Examples of the medicinal treatment methods include the use of antihistamines such as diphenhydramine, chlorpheniramine maleate, mectazine, ketotifen, azelastine, oxatomide, terfenadine or epinastine, and antiallergic agents such as tranilast or suplatast. Examples of the topical treatment methods include the use of moisturizers such as vaseline, urea or heparin, antihistamines such as diphenhydramine or chlorpheniramine maleate, steroids such as dexamethazone or hydrocortisone, antipruritic agents such as crotamiton, and local anesthetics such as dibucaine or lidocaine.

With respect to *acacia*, *acacia* honey is known, and tannin which is extracted from bark thereof is known to be able to be used as a tanning agent or a wood adhesive, while more recently, extracts of genus *Acacia* have been disclosed to have selective inhibitory effects on COX-2 (Patent Document 1), and bark of genus *Acacia* has been disclosed to have active oxygen eliminating effects (Patent Document 2) and skin whitening effects due to the effect of inhibiting tyrosinase activity (Patent Document 3). However, *acacia* bark and polyphenols derived from *acacia* bark have heretofore not been known to have any antipruritic effects.

[Patent Document 1] JP2004-532811A
[Patent Document 2] JP2004-352639A
[Patent Document 3] JP10-025238A

DISCLOSURE OF THE INVENTION

Problems to be Solved by the Invention

An object of the present invention is to provide a very safe and effective composition for the prevention and/or treatment of pruritus.

Means for Solving the Problems

As a result of conducting extensive studies to solve the above problems, the inventors of the present invention found that an *acacia* bark derivative has an excellent antipruritic effect, thereby leading to the completion of the present invention.

Namely, the present invention relates to a composition containing an *acacia* bark derivative(s) for the prevention and/or treatment of pruritus.

In addition, the present invention also relates to a method for preventing or treating pruritus using an *acacia* bark derivative(s).

Moreover, the present invention relates to a method for using an *acacia* bark derivative(s) for producing a composition for preventing or treating pruritus.

Effects of the Invention

Since the composition of the present invention prevents the onset of pruritus and cures or alleviates pruritus by demonstrating antipruritic and/or itching relief effects, it can be used for the prevention and/or treatment of pruritus.

In addition, the composition of the present invention is very safe and has less potential for adverse side effects and the like even if taken for a long period of time.

BEST MODE FOR CARRYING OUT THE INVENTION

There are no particular limitations on the *acacia* bark derivative able to be used in the present invention provided that it is obtained by using as a raw material bark of a tree belonging to the genus *Acacia* (the tree is referred to as "*acacia*" or "genus *Acacia*" hereinafter), examples of which derivatives include a strip and a powder of *acacia* bark, and a suspension thereof, an extract such as a liquid extract, a concentrated liquid extract and a powdered extract of *acacia* bark, and a purified product obtained by purifying these extracts. The extract of *acacia* bark and particularly *acacia* bark polyphenols are preferable for production of outstanding antipruritic effect.

In the present invention, only a single type of these *acacia* bark derivatives may be used, or alternatively two or more forms thereof may be used in combination.

Although there are no particular limitations on *acacia* able to be used in the present invention so long as it is a tree belonging to the genus *Acacia*, with respect to obtaining an *acacia* bark derivative having an excellent antipruritic effect, bark of the genus *Acacia* selected from the group consisting of scientific name: *Acacia mearnsii* De Wild. (generic name: black wattle), scientific name: *Acacia mangium* Willd. (generic name: *acacia mangium*), scientific name: *Acacia dealbata* Link, scientific name: *Acacia decurrens* Willd. and scientific name: *Acacia pycnantha* Benth. are preferable, while *Acacia mearnsii* De Wild. and *Acacia mangium* Willd. are particularly preferable.

In the present invention, only a single form of these *acacia* bark may be used, or alternatively two or more forms thereof may be used in combination.

The aforementioned *acacia* bark can normally be obtained by cutting down an *acacia* tree, pealing off only bark and then drying the bark more preferably by sun-drying.

Bark of *acacia* is comprised of an outer bark and a somewhat fibrous inner bark, and when dried to a moisture content of about 20% or less, can be easily finely pulverized with a size reducing mill such as a hammer mill. In the present invention, both the outer bark and inner bark of the genus *Acacia* may be used together or either one may be used alone as the *acacia* bark.

The aforementioned strip of *acacia* bark can be obtained in accordance with commonly used methods by pulverizing the *acacia* bark to a suitable size.

In addition, although the aforementioned powder of *acacia* bark can be obtained by pulverizing the *acacia* bark into a powder in accordance with commonly used methods, in particular, the particle diameter of the resulting powder is preferably 100 μm or less and particularly preferably 50 to 70 μm. Powder fractionation can be carried out by pulverizing the bark dried to a moisture content of 20% or less to a suitable size such as a particle diameter of about 1.6 mm or less, and then classifying the resulting powder with a vibrating screen or the like to obtain the required powder.

The aforementioned extract of *acacia* bark can be obtained by extraction from the *acacia* bark in accordance with commonly used methods. In order to obtain an extract of *acacia* bark having an excellent antipruritic effect, it is preferably extracted from the *acacia* bark with an alcohol or a polar solvent.

Ethanol, etc. can be used as the alcohol, and water, etc. can be used as the polar solvent, and these solvents may be used singly or in combination of two or more kinds as necessary. A mixed solvent of water and the alcohol such as ethyl alcohol is particularly preferable for production of excellent antipruritic effects.

Moreover, the extraction procedure may be carried out a number of times using the same or different solvents.

In terms of obtaining an extract having an excellent antipruritic effect, an extract which is obtained by extracting from the *acacia* bark with water or hot water, and then further extracting from the resulting extract with ethanol may be used.

Although the extraction is carried out by adding the solvent to a strip, a powder or the like of the *acacia* bark followed by stirring as necessary, there are no particular limitations on temperature, time or solid-liquid ratio. In the case of using water as the solvent, the extraction may also be carried out with hot water. The resulting liquid extract may be freeze-dried or spray-dried directly, or may be freeze-dried or spray-dried after concentrating under reduced pressure. The resulting extract can be in various forms, such as a liquid extract, solution, powder, concentrate or paste, and can be used in a wide range of forms as necessary.

Moreover, the *acacia* bark extract of the present invention obtained in any of these forms can be used directly for the prevention or treatment of pruritus, or a purified product obtained by purifying the extract as necessary can also be used as an antipruritic active ingredient.

In the present invention, ingredients contained in bark of the genus *Acacia* are also examples of the *acacia* bark derivatives. Examples of such ingredients are the *acacia* bark polyphenols. The *acacia* bark polyphenols are particularly preferable ingredients since they produce excellent antipruritic effects.

The *acacia* bark polyphenols of the present invention refer to a type of condensed tannins in the form of polymers in which flavanols having as a basic skeleton flavan-3-ol such as (−)-fisetinidol, (−)-robinetinidol, (+)-catechin and (+)-gallocatechin are linked by C4-C8 or C4-C6 bonds. Here, the molecular weights of such condensed tannins are preferably 300 to 3000 and particularly preferably 500 to 3000. The *acacia* bark polyphenols used in the present invention can be obtained from the powder, etc. of the *acacia* bark by extraction with hot water as previously described.

In addition, examples of commercially available *acacia* bark polyphenols include MIMOSA ME POWDER, MIMOSA MS POWDER, MIMOSA GS POWDER, MIMOSA FS POWDER, MIMOSA WS POWDER, MIMOSA RG POWDER, MIMOSA RN POWDER, MIMOSA DK POWDER, MIMOSA AL POWDER, MIMOSA CR POWDER and GOLDEN MIMOSA POWDER (all registered trademarks) which are manufactured by Mimosa Central Co-operative Ltd., and the like.

Although the composition of the present invention may be the *acacia* bark derivative(s) such as the *acacia* bark, the extract(s) thereof, the purified product(s) thereof or the *acacia* bark polyphenol(s) per se, it may also contain other substance(s) having an antipruritic effect such as antihistamines such as crotamiton, antiallergics, tumeric, tienchi ginseng, KW lactobacillus, maca or mugwort lotion. Antihistamines, antiallergics, tumeric, tienchi ginseng or KW lactobacillus are particularly preferably contained since they produce excellent antipruritic effects due to synergistic effects.

Although the composition of the present invention may be the *acacia* bark derivative(s) such as the *acacia* bark, the extract(s) thereof, the purified product(s) thereof or the *acacia* bark polyphenol(s) per se, it may contain vehicles, sweeteners, sour flavorings, thickeners, fragrances, pigments, emulsifiers, and other additives or materials which are ordinarily used in drugs or foods, so long as they do not undermine the effects of the present invention.

The composition of the present invention can be used to prevent or treat pruritus. Examples of such pruritus include skin itching accompanying skin diseases such as eczema, dermatitis, urticaria, prurigo nodularis and essential pruritus. Specific examples include skin itching accompanying skin diseases such as atopic dermatitis, contact dermatitis, housewives eczema, hand eczema, diaper dermatitis, seborrheic dermatitis, senile pruritus, prurigo nodularis, rash, senile xerosis, asteatotic eczema, insect bites, tinea cruris, tinea pedis and blepharitis accompanying pollen allergies. In addition, the composition of the present invention is also useful for notalgia paresthetica, itching caused by hemodialysis for treatment of kidney failure, and psoriasis accompanied by itching.

In particular, the composition of the present invention is useful against pruritus caused by immunity abnormalities such as allergies, examples of which include urticaria, atopic dermatitis, contact dermatitis and blepharitis accompanying pollen allergies, and particularly against atopic dermatitis and blepharitis accompanying pollen allergies.

Furthermore, in the present invention, treatment includes the elimination, alleviation of symptoms, curing and suppression of exacerbation of pruritus.

There are no particular limitations on an ingested amount of the composition according to the present invention, and the ingested amount can be suitably selected depending on the dosage form as well as the age, body weight and symptoms of an ingesting person such as a user or patient, or an ingesting animal. For example, it is desired that the ingesting person or ingesting animal orally ingests an amount of the *acacia* bark polyphenol(s) ranging from 0.001 to 1 g, preferably from 0.001 to 0.5 g and more preferably from 0.005 to 0.1 g per 1 kg of body weight per day in terms of the amount of active ingredient, since it produces an excellent antipruritic effect.

The duration of ingestion can be arbitrarily determined depending on the age and symptoms of the ingesting person or ingesting animal.

The composition according to the present invention can be used as a food or an animal feed material, for example, as a health food, a functional food, a health supplement food, a food for specified health use, a beauty food or a nutritional supplement food (supplement). For example, these foods or animal feed material may also be in the form of a beverage such as tea or juice; ice cream, jelly, candy, chocolate or chewing gum, etc. In addition, they may also be in the form of liquids, powders, granules, capsules or tablets. Here, animals fed by the animal feed material include all animals requiring the prevention or treatment of pruritus, including pets, livestock or animals bred at zoos, etc.

In addition, the composition according to the present invention can be used as a medicine or a quasi-drug. Although the medicine or quasi-drug can be administered, for example, orally in the form of powders, tablets, coated tablets, sugar coated pills, hard or soft gelatin capsules, liquids, emulsions or suspensions, they can also be administered parenterally, such as rectally in the form of suppositories, or such as topically or percutaneously in the form of ointments, creams, gels or liquids.

Although the following provides a more detailed explanation of the present invention through examples thereof, the present invention is not limited thereto.

EXAMPLES

Although the following provides a more detailed explanation of the present invention through production examples, test examples and formulation examples thereof, the present invention is not limited thereto. In particular, although the following examples are indicated without making a distinction between the outer bark and inner bark of the *acacia* bark of the present invention, the outer bark can be separated from the inner bark and each can also be used, separately.

In the following production examples, test examples and the like, each *acacia* of the present invention is indicated with numbers shown in parentheses after each scientific name. For example, *acacia* known by the scientific name of *Acacia mearnsii* De Wild. is indicated as *Acacia* No. 1.

Scientific name: *Acacia mearnsii* De Wild. (No. 1), scientific name: *Acacia mangium* Willd. (No. 2), scientific name: *Acacia dealbata* Link (No. 3), scientific name: *Acacia decurrens* Willd. (No. 4), scientific name: *Acacia pycnantha* Benth. (No. 5).

In addition, percentages (%) refer to percent by weight (wt %) unless specifically indicated otherwise.

Production Example 1

*Acacia* Bark Powder

Bark of *Acacia* No. 1 was dried to a moisture content of 20% or less and after pulverizing the dried bark in a hammer mill to a powder having a particle diameter of 1.6 mm or less (the powder passing through a 10 mesh Tyler screen), the powder was further classified with a vibrating screen to obtain a fine powder having a particle diameter of 63 μm or less (passing through a 250 mesh screen).

Fine powders each having a particle diameter of 63 μm or less were similarly obtained by pulverizing bark of the remaining four types of *acacia* namely *Acacia* No. 2 to *Acacia* No. 5. Although there were some differences in the efficiency by which the fine powder passed through the 250 mesh screen depending on the type, all of the target fine powders were able to be obtained.

Production Example 2

*Acacia* Bark Extract

Bark of each *Acacia* No. 1 to 5 of the present invention was dried to a moisture content of 20% or less and after pulverizing the dried bark in a hammer mill to a powder having a particle diameter of 1.6 mm or less, five times the amount of hot water were added to 100 g of the dried pulverized bark followed by extraction for 15 minutes after boiling, and then filtering using a 10 to 20 μm filter. The resulting filtrate was spray-dried in a spray dryer to obtain 40 g of each bark extract.

The bark extracts are hereinafter indicated as *Acacia* Hot Water Extracts Nos. 1 to 5, respectively.

Production Example 3

*Acacia* Bark Extract

*Acacia* bark of the present invention was dried to a moisture content of 20% or less and after pulverizing the dried bark in a hammer mill to a powder having a particle diameter of 1.6 mm or less, five times the amount of ethanol were added to 100 g of the dried pulverized bark followed by extracting for 15 minutes while refluxing after boiling, and then filtering using a 10 to 20 μm filter. After evaporating the ethanol from the resulting filtrate, the concentrate was spray-dried in a closed spray dryer to obtain 40 g of bark extract (to be indicated hereinafter in the manner of *Acacia* Ethanol Extract No. 1).

*Acacia* Ethanol Extracts Nos. 1 to 5 were obtained in the same manner.

Production Example 4

*Acacia* Bark Extract

Three times the amount of ethanol were added to 10 g of the *acacia* hot water extract obtained in Production Example 2 followed by extraction for 15 minutes while refluxing after boiling, and then filtering using a 10 to 20 μm filter. The ethanol was evaporated from the resulting filtrate, water was added thereto, and then freeze-dried to obtain 9 g of extract (to be indicated hereinafter in the manner of *Acacia* Hot Water Extract Ethanol Fraction No. 1).

*Acacia* Hot Water Extract Ethanol fractions Nos. 1 to 5 were obtained in the same manner.

Test Example 1

Skin Itching Behavior Suppression Test (1)

(1) Test Method

The required weighed amount of *Acacia* Hot Water Extract No. 1 described in the aforementioned Production Example 2 was mixed into ordinary feed to prepare a test feed 1 containing 1.5% of *Acacia* Hot Water Extract No. 1.

5-week-old ddY mice were assigned to three groups (6 to 8 mice per group) consisting of Ordinary Feed group, Compound treatment group and Test Feed 1 group. Animals in the Ordinary Feed group and Compound treatment group were given ordinary feed, while animals of the Test Feed 1 group were given test feed 1.

Itching behavior of the mice was measured on day 28 (week 4), day 35 (week 5) and day 42 (week 6) after the start of the ingestion of the feed. Compound 48/80 (Sigma) was administered subcutaneously to animals of the Compound Treatment group and Test Feed 1 group at 0.5 mg/kg (20 μg/animal). Next, the mice were individually placed in plastic containers and itching behavior of the mice were recorded on video for 30 minutes after administration of the Compound 48/80. The number of times the mice demonstrated itching behavior was counted by observing the recorded video. Itching behavior was categorized into three types consisting of scratching the neck and back with the left or right hind limb (scratching), grooming the head with a fore limb (grooming) and licking from the abdomen to the back (licking), and the total number of each type of itching behavior was counted at five minute intervals.

The resulting measured values were expressed as the mean±standard error. Testing for homogeneity of variance was carried out using Bartlett's method, and the results were further tested by ANOVA in the case of equal variance. A comparison of mean values was additionally carried out using Tukey's method only in the case of a significant result with ANOVA. In the case of unequal variance distribution as determined with Bartlett's method, the results were tested using the Kruskal-Wallis H-test, and a comparison of mean values was additionally carried out using Tukey's method only in the case significance was observed. The level of significance was indicated as 5%.

(2) Test Results

The results are shown in Table 1.

TABLE 1

| Action of Test Feed on Itching Behavior | | | | |
|---|---|---|---|---|
| Itching behavior | Measurement day | Ordinary Feed group | Compound Treatment group | Test Feed 1 group |
| Scratching | Week 4 | 21.0 ± 10.9 | 31.6 + 17.6 | 13.3 ± 7.1 (57.9) |
| | Week 5 | 14.5 ± 7.6 | 53.4 ± 16.2 | 29.6 ± 9.9 (44.6) |
| | Week 6 | 27.8 ± 9.3 | 66.8 ± 14.8 | 50.0 ± 18.0 (25.1) |
| Grooming | Week 4 | 22.0 ± 3.1 | 24.4 ± 3.2 | 25.3 ± 5.2 (−3.69) |
| | Week 5 | 24.5 ± 1.7 | 29.0 ± 2.9 | 19.1 ± 3.7 (34.1) |
| | Week 6 | 34.7 ± 8.2 | 30.5 ± 1.8 | 26.8 ± 7.3 (12.1) |
| Licking | Week 4 | 22.2 ± 2.1 | 22.9 ± 2.1 | 16.3 ± 2.8 (28.8) |
| | Week 5 | 21.8 ± 3.1 | 24.1 ± 1.3 | 11.8 ± 2.8** (51.0) |
| | Week 6 | 28.0 ± 4.9 | 25.1 ± 2.3 | 18.1 ± 4.4 (27.9) |

( ): Indicates rate of decrease (%) versus Compound Treatment group
**Comparison with Compound Treatment group. It shows P < 0.01.

Test Example 2

Skin Itching Behavior Suppression Test (2)

(1) Test Method

This test was carried out in compliance with the method described in Makiura, M., et al: J. Int. Med. Res., 2004, 32(4): 392-399.

The required weighed amount of *Acacia* Hot Water Extract No. 1 described in the aforementioned Production Example 2 was mixed into a special feed (HR-AD Purified Feed, Nosan Corp.) to respectively prepare mixed test feeds containing 0.5%, 1.5% and 5.0% of *Acacia* Hot Water Extract No. 1.

5-week-old Hos:HR-1 male mice (acquired from Hoshino Laboratory Animals Co., Ltd.) were assigned to five groups (of 6 to 8 animals each). Each group respectively was fed an ordinary feed, the special feed or the *Acacia* Hot Water Extract No. 1 mixed feed.

The itching behavior of the mice was recorded on video for 30 minutes on day 28 (week 4), day 35 (week 5) and day 42 (week 6) after the start of ingestion of feed. The number of times the mice demonstrated itching behavior was counted in the same manner as Test Example 1 by observing the recorded video.

Measured values were expressed as the mean±standard deviation.

(2) Test Results

The results of counting the total number of incidences of itching behavior for each type of itching are shown in Table 2.

TABLE 2

| Action of Test Feed on Itching Behavior | | | | | | |
|---|---|---|---|---|---|---|
| Itching behavior | Measurement day | Ordinary Feed group | Special Feed group | *Acacia* Hot Water Extract No. 1 Mixed Test Feed groups | | |
| | | | | 0.5% | 1.5% | 5.0% |
| Scratching | Week 4 | 34.0 ± 15.2 | 77.9 ± 18.7 | 67.8 ± 18.0 (13.0%) | 39.5 ± 10.1 (49.3%) | 98.5 ± 17.0 (−26.4%) |
| | Week 5 | 49.0 ± 12.3 | 106.4 ± 21.1 | 129.8 ± 29.9 (−22.0%) | 72.8 ± 17.3 (31.6%) | 162.0 ± 29.4 (−52.3%) |
| | Week 6 | 15.8 ± 2.9 | 76.9 ± 17.0 | 123 ± 31.9 (−59.9%) | 72.5 ± 17.1 (5.7%) | 104.9 ± 28.5 (−36.4%) |
| Grooming | Week 4 | 14.8 ± 2.6 | 33.3 ± 6.1 | 30.0 ± 4.3 (9.9%) | 22.6 ± 3.7 (32.1%) | 25.8 ± 4.6 (22.5%) |
| | Week 5 | 35.7 ± 6.3 | 40.0 ± 5.1 | 41.0 ± 5.8 (−2.5%) | 37.8 ± 5.5 (5.5%) | 43.9 ± 5.7 (−9.7%) |
| | Week 6 | 18.3 ± 2.0 | 25.6 ± 4.0 | 26.5 ± 4.5 (−3.5%) | 23.3 ± 3.2 (9.0%) | 25.0 ± 4.1 (2.3%) |
| Licking | Week 4 | 18.7 ± 2.9 | 24.5 ± 3.7 | 25.4 ± 2.1 (−3.7%) | 19.9 ± 2.4 (18.8%) | 20.8 ± 2.3 (15.1%) |
| | Week 5 | 40.3 ± 3.1 | 36.5 ± 4.6 | 37.1 ± 7.6 (−1.6%) | 30.0 ± 3.3 (17.8%) | 25.8 ± 5.7 (29.3%) |
| | Week 6 | 18.2 ± 1.6 | 27.3 ± 2.9 | 28.5 ± 4.9 (−4.4%) | 23.4 ± 2.9 (14.3%) | 22.4 ± 3.5 (17.9%) |

( ): Indicates rate of decrease (%) versus Special Feed group

On the basis of Test Examples 1 and 2, the *acacia* bark polyphenols were shown to be effective against skin itching.

Test Example 3

Mutagenicity Test

A mutagenicity test was conducted in compliance with the Ministry of Health, Labor and Welfare Notification No. 77 (Sep. 1, 1988). As a result of testing with test substance (*Acacia* Hot Water Extracts Nos. 1 to 5 of Production Example 2) at doses of 156 to 5,000 μg/plate, there were no increases in the numbers of revertant colonies for any of the bacterial strains.

Test Example 4

Micronucleus Test

The presence of the ability to induce micronuclei was investigated in vivo in accordance with ordinary methods. *Acacia* Hot Water Extract No. 1 was orally administered twice at 24-hour intervals at daily doses of 2,000, 1,000 and 500 mg/kg to male ICR mice followed by the preparation of micronucleus specimens 24 hours after the final dosing.

*Acacia* Hot Water Extract No. 1 did not demonstrate positive results at any of the dose levels. In addition, there were no constant fluctuations in the simultaneously observed ratio of total polychromatic erythrocytes to total erythrocytes, and inhibition of erythrocyte proliferation was not observed in comparisons with a negative control group.

Test Example 5

Mouse Acute Toxicity Study (Oral Administration)

An acute oral dose toxicity study was conducted using male and female ICR mice in compliance with OECD (Guidelines for the Testing of Chemicals, 401, 1987). As a result, the $LD_{50}$ value of *Acacia* Hot Water Extract No. 1 was 4,468 mg/kg among males and 3,594 mg/kg among females.

Similar results were obtained in the above study for *Acacia* Hot Water Extracts Nos. 2 to 5 of Production Example 2.

Test Example 6

Rat Repeated Dose Toxicity Study (Oral Administration)

A 13-week repeated dose toxicity study was conducted using rats in accordance with ordinary methods. Mixed feed containing 0.5, 1.5 and 5.0% of *Acacia* Hot Water Extract No. 1 was fed to male and female Slc:SD rats.

As a result, none of the rats died or demonstrated abnormalities in examinations, including general condition.

Test Example 7

Human Single Dose Study

Five healthy adult males age 32 to 43 years were given 1500 mg of *Acacia* Hot Water Extract No. 1 (12 tablets of Formulation Example 4 described below). Although general examinations, hematology tests, blood biochemistry tests and urinalyses were performed on the subjects before ingestion, 3 hours after ingestion, 8 hours after ingestion, 24 hours after ingestion and 1 week after ingestion, there were no clinically significant fluctuations in test values. There were also no adverse events attributable to the tablets.

Test Example 8

Human 4-Week Continuous Dosing Study

Twenty-five healthy adult males age 23 to 44 years were given *Acacia* Hot Water Extract No. 1 of Formulation Example 4 described below at 750 mg/day (6 tablets of Formulation Example 4) and 1000 mg/day (8 tablets of Formulation Example 4) for 4 weeks each.

General examinations, hematology tests and urinalyses were performed on the subjects of each group before ingestion, 2 weeks after ingestion, 4 weeks after ingestion and 2 weeks following completion of ingestion. There were no clinically significant fluctuations in test values. There were also no adverse events.

Formulation Example 1

Preparation of Internal Medication

An internal medication having the composition indicated below was prepared using the *acacia* bark Hot Water Extract Ethanol Fraction of Production Example 4.

| | |
|---|---|
| Extract fraction of Production Example 4 | 1.0 (wt %) |
| Lactose | 30.0 |
| Cornstarch | 60.0 |
| Crystalline cellulose | 8.0 |
| Polyvinyl pyrrolidone | 1.0 |
| Total | 100.0 |

Formulation Example 2

Preparation of Pet Food

A pet food having the composition indicated below was prepared using the *acacia* bark Hot Water Extract of Production Example 2,

| | |
|---|---|
| Extract of Production Example 2 | 1.0 (wt %) |
| Oatmeal | 88.0 |
| Starch | 5.0 |
| Salt | 2.5 |
| Whole egg | 3.0 |
| Flavoring | 0.5 |
| Total | 100.0 |

Formulation Example 3

Preparation of Tablets (Confections)

Tablets (confections) having the composition indicated below were prepared using the *acacia* bark Hot Water Extract Ethanol Fraction of Production Example 4.

| | |
|---|---|
| Extract fraction of Production Example 4 | 1.0 (wt %) |
| Citric acid | 1.0 |
| Powdered skim milk | 15.0 |
| Sucrose ester | 1.0 |
| Flavoring | 0.5 |
| Powdered sugar | 20.0 |
| Lactose | 61.5 |
| Total | 100.0 |

Formulation Example 4

Preparation of Tablets

Tablets having the composition indicated below were prepared using *Acacia* Bark Hot Water Extract No. 1 of Production Example 2.

| | |
|---|---|
| Acacia Bark Hot Water Extract No. 1 of Production Example 2 | 125 (mg) |
| Sucrose ester | 9 |
| Lactose | 166 |
| Total | 300 |

INDUSTRIAL APPLICABILITY

According to the present invention, a composition for preventing and/or treating pruritus can be obtained.

More specifically, the composition of the present invention is useful for preventing and/or treating pruritus associated with allergic diseases.

This composition can be used as a medicine, a quasi-drug or a cosmetic, or as a food or an animal feed material such as a health food, a health supplement food, a food for specified health use or a nutritional supplement food.

The invention claimed is:

1. A method of treating pruritus in a patient having an immunity abnormality which comprises treating said patient with a composition containing a therapeutically effective amount of an *Acacia mearnsii* De Wild bark extract.

2. The method of claim 1, wherein the bark extract comprises an *acacia* bark polyphenol(s).

3. The method of claim 2, wherein the *acacia* bark polyphenol(s) is a condensed tannin(s).

4. The method of claim 3, wherein the condensed tannin(s) has a molecular weight(s) of 500 to 3000.

5. The method of claim 3, wherein the condensed tannin(s) is a polymer(s) of flavanols having flavan-3-ol as a basic skeleton.

6. The method of claim 2, wherein the *acacia* bark polyphenol(s) is orally ingested by said patient at 0.001 to 1 g per kg of body weight of the patient per day.

7. The method of claim 1, wherein the composition is a food.

8. The method of claim 1, wherein the composition is a medicine, a quasi-drug, an animal feed material or a cosmetic.

* * * * *